United States Patent [19]

Xavier

[11] Patent Number: 5,251,641
[45] Date of Patent: Oct. 12, 1993

[54] BIOPSY NEEDLE

[75] Inventor: Alfredo F. Xavier, New Bedford, Mass.

[73] Assignee: HGG Laser Fare, Inc., Smithfield, R.I.

[21] Appl. No.: 921,338

[22] Filed: Jul. 29, 1992

[51] Int. Cl.$^5$ .............................................. A61B 10/00
[52] U.S. Cl. .................................... 128/754; 606/170
[58] Field of Search ....................... 128/751, 753, 754; 606/167, 170

[56] References Cited

U.S. PATENT DOCUMENTS

| | | | |
|---|---|---|---|
| 1,493,240 | 5/1924 | Bohn | 606/170 |
| 2,516,492 | 7/1950 | Turkel | |
| 2,749,909 | 6/1956 | Ullery et al. | |
| 2,827,039 | 3/1958 | Seiger | |
| 3,330,268 | 7/1967 | Goldsmith | |
| 3,732,858 | 5/1973 | Banko | |
| 3,844,272 | 10/1974 | Banko | |
| 3,929,123 | 12/1975 | Jamshidi | |
| 4,513,754 | 4/1985 | Lee | 128/753 |
| 4,543,966 | 10/1985 | Islam et al. | 128/754 |
| 4,609,370 | 9/1986 | Morrison | 128/754 |
| 4,640,296 | 2/1987 | Schnepp-Pesch | 128/754 |
| 4,702,260 | 10/1987 | Wang | 128/753 |
| 4,708,147 | 11/1987 | Haaga | 128/753 |
| 4,799,494 | 1/1989 | Wang | 128/753 |
| 4,926,877 | 4/1990 | Bookwalter | 128/754 |

OTHER PUBLICATIONS

Westcott, Biopsy Needle, Becton Dickinson advertisement, 1991.

Primary Examiner—Max Hindenburg
Attorney, Agent, or Firm—Ross, Ross & Flavin

[57] ABSTRACT

A biopsy needle which contains a rotating and axially removable inner cannula housed within an outer cannula in the form of a penetrating needle, the configuration allowing for the removal of multiple tissue specimens with a single needle insertion, with a minimized risk of trauma to surrounding tissue, the distal ends of the outer and inner cannulas containing coextensive open channels, the outer and inner cannulas having operative distal piercing ends defined by converging lateral piercing edges interconnected inferiorly by a semiconical transverse base surface, and superiorly by trailing semicircumferential cutting edges, angled with reference to the needle horizontal axis, the inner cannula having an operative 180° rotary motion around the common longitudinal axis of the inner and outer cannulas, said rotary action performing the transverse cutting of tissue entrapped within the open distal chamber of the needle, the procedure being performed without the need for suction or irrigation, in such a manner that the structural integrity of the specimen is uniquely preserved.

10 Claims, 2 Drawing Sheets

BIOPSY NEEDLE

BACKGROUND OF THE INVENTION

1. Field of the Invention

The invention relates to biopsy needles for extracting human tissue specimens.

2. Description of the Prior Art

The prior art of which I am aware is listed on the enclosed form PTO-1449. None of the prior art is adapted for end cutting, side cutting and extracting of tissue specimens, the procedure being performed without the need for suction or irrigation and in such a manner that the structural integrity of the specimen is uniquely preserved.

SUMMARY OF THE INVENTION

The biopsy needle hereof includes a rotating and axially removable inner cannula housed within an outer cannula in the form of a penetrating needle, the configuration allowing for the removal of multiple tissue specimens with a single needle insertion, with a minimized risk of trauma to surrounding tissue, the distal ends of the outer and inner cannulas containing coextensive open channels, the outer cannula having an operative distal piercing end defined by converging lateral piercing edges interconnected inferiorly by a semiconical transverse base surface, and superiorly by a trailing semicircumferential cutting edge, angled forwardly with reference to the needle horizontal axis.

The inner cannula has an identical coaxial operative distal end which may be telescoped into the distal end of the outer cannula, the inner cannula also containing converging lateral cutting edges, connected inferiorly by a semiconical transverse base surface, the superior surface containing a semicircumferential edge which is angled rearwardly with reference to the needle horizontal axis.

The inner cannula has an operative 180° rotary motion around the common longitudinal axis of the inner and outer cannulas, said rotary action performing the transverse cutting of tissue entrapped within the open distal specimen chamber of the needle, the procedure being performed without the need for suction or irrigation, in such a manner that the structural integrity of the specimen is uniquely preserved.

Both inner and outer cannulas have proximal handheld ends provided with engaging knobs for the control of the operation of the assembled device.

DESCRIPTION OF THE PREFERRED EMBODIMENTS

Figure 1:
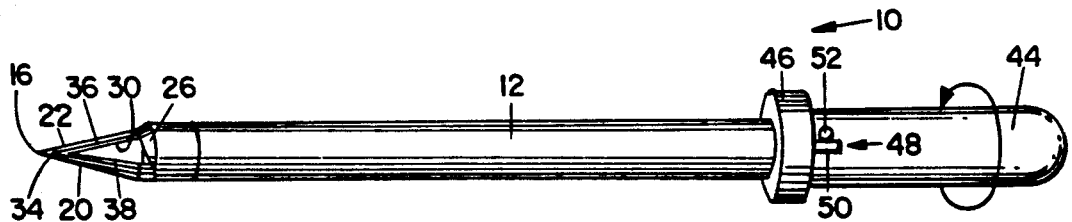
FIG. 1 is a top perspective view of a biopsy needle embodying a preferred form of the invention, with an inner cannula telescopically and rotatably fitted within an outer cannula and jointly defining a tissue sampling chamber.
Figure 2:
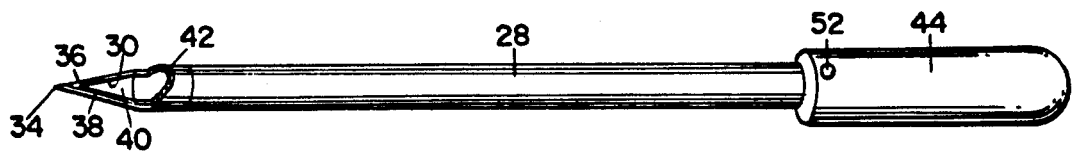
FIG. 2 is a top perspective view of the inner cannula of the biopsy needle.

A biopsy needle 10 adapted for end cutting, side cutting and extracting of tissue specimens includes a cylindrical hand held outer cannula 12 having an open, tubular longitudinal channel 14 and a wedge shaped semi-conical hollow piercing tip 16, the piercing tip having an open distal channel 18 in continuity with open longitudinal channel 14.

Wedge shaped hollow piercing tip 16 is defined by two converging lateral cutting surfaces 20 and 22 interconnected inferiorly by a transverse semi-conical base surface 24 and interconnected superiorly by a semicircumferential cutting edge 26 angled forwardly with reference to the longitudinal axis of the cannula toward its distal end.

A hand held inner cannula 28 is telescopically and rotatably fitted within outer cannula 12 and has an open distal channel 30 co-extensive with distal channel 18 of the outer cannula, the open distal channels 18 and 30 jointly defining a tissue sampling chamber 32, as will appear.

Inner cannula 28 has a semi-conical hollow piercing tip 34 defined by two converging lateral cutting surfaces 36 and 38, interconnected inferiorly by a semi-conical transverse base surface 40 and interconnected superiorly by a semi-circumferential cutting edge 42 angled rearwardly toward the posterior of the needle with reference to the longitudinal axis of the cannula, toward the proximal end of the cannula.

Both inner and outer cannulas have proximal handheld ends provided with engaging knobs 44 and 46 respectively, for the control of the operation of the assembled device.

Positive stop means 48 is provided to signal complete 180° rotation of inner cannula 28 relative to outer cannula 12 and includes a pin 50 which extends longitudinally rearwardly from engaging knob 46 of outer cannula 12 and a pin 52 which extends transversely outwardly from engaging knob 44 of inner cannula 28.

Pins 50 and 52 are of suitable length as to contact each other upon rotation of the inner cannula through a 180° arc to provide a positive stop.

Biopsy needle 10 is defined by rotatable and axially removable inner cannula 28 housed within outer cannula 12, the cannulas forming a penetrating needle, the configuration allowing for the removal of multiple tissue specimens with a single needle insertion, with a minimized risk of trauma to surrounding tissue.

Inner cannula 28 has an operative 180° rotary motion around the common longitudinal axis of the inner and outer cannulas, said rotary action performing the transverse cutting of tissue entrapped within the open distal chamber 30 of the needle, the procedure being performed without the need for suction or irrigation, in such a manner that the structural integrity of the tissue specimen is uniquely preserved.

Biopsy needle 10 has three sequential and reversible modes of operation namely, a closed-tip piercing operational mode, a longitudinal cutting mode, and a transverse cutting mode defined by the procedure of rotating inner cannula 28 within outer cannula 12.

Figure 6:
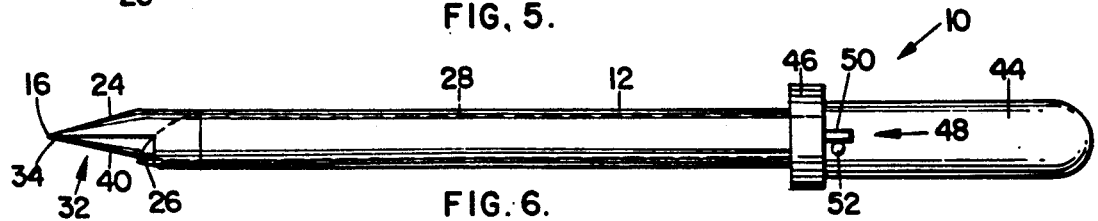
FIG. 6 is a side elevational view of the assembled inner and outer cannulas of the biopsy needle, the inner cannula having been rotated 180° to fully enclose the tissue sampling chamber.
Figure 7:
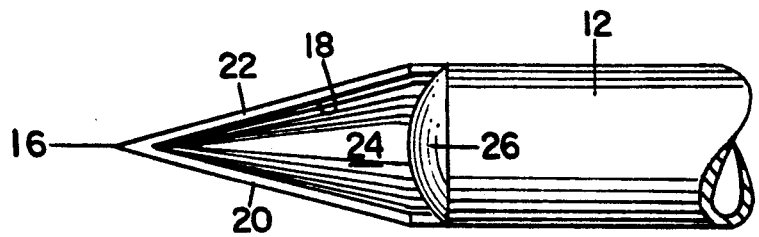
FIG. 7 is a greatly enlarged, fragmentary, top plan view of the outer cannula.
Figure 8:
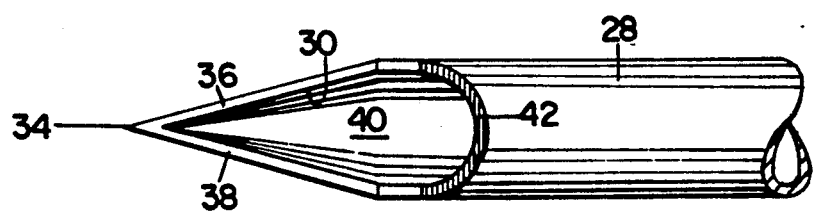
FIG. 8 is a greatly enlarged, fragmentary, top plan view of the inner cannula.
Figure 10:
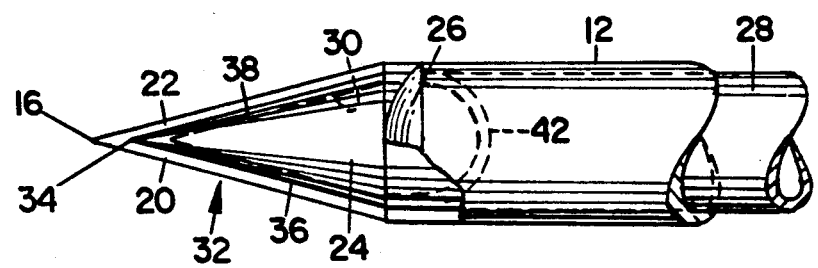
FIG. 10 is a view similar to FIG. 9, the inner cannula having been rotated 180° to fully enclose the tissue sampling chamber.

The closed-tip piercing operational mode is achieved through the rotation of inner cannula 28 within outer cannula 12 such that they are in an inverse relationship with regard to their geometric features, as shown in FIGS. 6 and 10, with such alignment of the cannulas producing an effective conical shape facilitating the piercing of tissue during needle insertion, while avoiding the entrapment of random samples.

Figure 9:
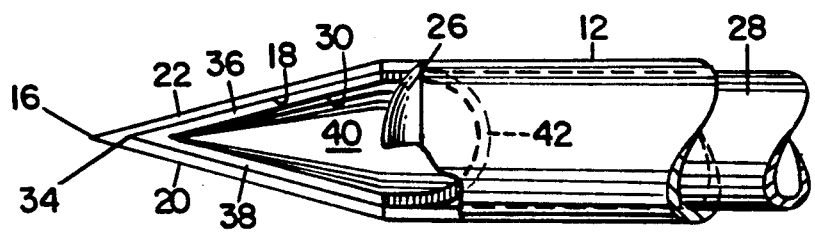
FIG. 9 is a greatly enlarged, fragmentary top plan view of the inner cannula telescopically and rotatably fitted within the outer cannula and jointly defining a tissue sampling chamber.

The longitudinal cutting mode is achieved through the rotation of inner cannula 28 within outer cannula 12 such that the semiconical distal ends 34 and 16 respectively of the cannulas are aligned in a contiguous manner as shown in FIGS. 1 and 9, with piercing tip 36 of inner cannula 28 fitting precisely within piercing tip 16 of outer cannula 12 thereby opening the longitudinal channel 30 within the two cannulas with longitudinal cutting being accomplished by the two converging lateral surfaces 36 and 38, as well as by the forward advancing superior edge 26 of a outer cannula as the needle is advanced in the aforementioned open position into the desired tissue by means of forward motion along the horizontal axis of the biopsy needle.

The transverse cutting mode is achieved sequentially following the longitudinal entrapment of the specimen tissue through the 180° rotation of inner cannula 28 within outer cannula 12, whereby upon completion of the transverse cutting process, a three dimensional specimen, not shown, is severed and entrapped within the interior diameter of the inner and outer cannulas, whose alignments are now inversely related, as shown in FIGS. 6 and 10, with minimized risk of structural damage to the specimen due to crushing or ripping.

Inner cannula 28 performs the transverse cutting of tissue as outer cannula 12 remains in a stationary position, thereby minimizing traumas to adjacent anatomical structures while enhancing the accuracy of the tissue sample.

STEPS FOR SECURING A CORE TISSUE BIOPSY

1. The operational end of needle 10 is manually rotated to achieve the conical piercing mode of FIGS. 6 and 10. Conical piercing tip 16 is then inserted through the skin by applying gentle forward pressure to hand held proximal knob 44. Due to the piercing characteristics of the conical tip, rotation of the needle is not necessary. The use of a local anesthetic will provide for painless skin penetration.

After penetration, the needle shaft is directed to the specimen site, as the opposite hand of the operator palpates the target point and functions as a guide.

2. The needle is advanced in its closed piercing mode to the periphery of the specimen site. The solid configuration of the conical tip during insertion prevents the inadvertent collection of unwanted materials as the needle is inserted through intermediate tissue.

3. As the needle tip reaches the periphery of the specimen, as perceived by the operator's hands or by imaging techniques, inner cannula 28 is rotated counterclockwise 180° into the longitudinal cutting mode. In this configuration, the operational distal end presents a semi-conical configuration, with hollow tissue entrapment chamber 30 of inner cannula 28 in an open position.

4. The needle tip is next advanced into the desired specimen tissue through a forward motion along a longitudinal axis for a distance generally equivalent to the length of specimen chamber 32. This forward motion performs the longitudinal cutting of the desired tissue as it is advanced into specimen chamber 32. This cutting action is performed by the inferior converging semi-conical tip 24 in conjunction with the forward advancing semi-cylindrical superior cutting edge 42.

Upon completion of this step, the specimen is housed within chamber 32, but is still attached to the donor tissue by means of a cylindrical stem along its longitudinal axis, at the extreme distal end of the biopsy needle.

5. To completely sever and isolate the specimen from its donor source, inner cannula 28 is now rotated 180° clockwise. This rotary motion will transsect the remaining longitudinal tissue attachment in an inclined, transverse manner. This transverse cutting action completes the three dimensional separation of the specimen from its donor tissue. Further, the specimen is isolated within the cylindrical volume of the inner and outer cannulas, which are now configured in an oppositional alignment, thus returning the needle to its closed conical configuration as seen in FIGS. 6 and 10.

6. The isolated specimen is extracted from the assembly by the withdrawal of inner cannular 28 from outer cannula 12. During this phase, inner cannula 28 remains in the closed position achieved during the final transection of the specimen, and outer cannula 12 remains stationary within the donor tissue. Inner cannula 28 is manually withdrawn by gently pulling on proximal handle 44 in a backward direction along a longitudinal axis.

7. Additional specimens may then be obtained by simply reintroducing inner cannula 28 in the open position, into outer cannula 12. Open distal chamber 30 is then advanced slightly further into the donor tissue to push a new sample into the cylindrical chamber. As before, the tissue is then transversely severed by means of a 180° clockwise rotation of inner cannula 28 within the outer cannula 12. Once again, the specimen is removed by withdrawing the inner cannula, in the closed position, while the outer cannula remains stationary within the donor tissue.

8. This procedure may be repeated indefinitely at the discretion of the operator until a satisfactory volume of specimen is removed. Once a sufficient volume of tissue has been extracted, the entire assembly is removed.

Figure 11:
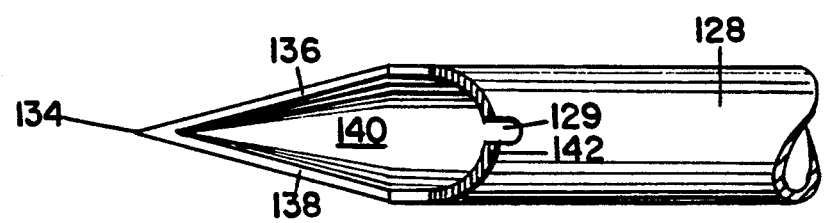
FIG. 11 is a greatly enlarged, fragmentary, top plan view of a first modified form of inner cannula.

In the modified form of FIG. 11, an inner cannula 128 is provided with a notch 129 located at the posterior end of a superior semi-circumferential cutting edge 142, which interconnects two converging lateral cutting surfaces 136 and 138 interconnected inferiorly by a semi-conical transverse base surface 140 and defining a semi-conical piercing tip 134.

Notch 129 facilitates the removal of a tissue specimen from the tissue sampling chamber.

Figure 3:
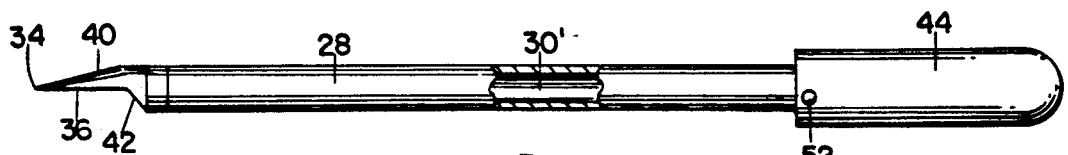
FIG. 3 is a side elevational view of the inner cannula of FIG. 2 rotated 180°, with parts broken away for clarity.
Figure 4:
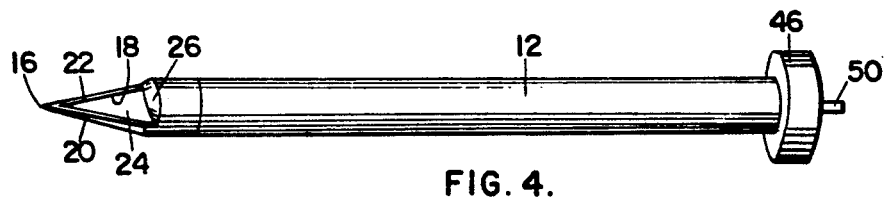
FIG. 4 is a top perspective view of the outer cannula of the biopsy needle.
Figure 5:
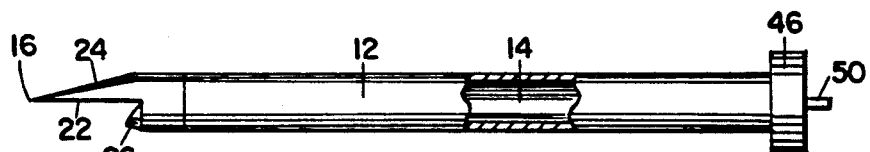
FIG. 5 is a side elevational view of the outer cannula of FIG. 4 rotated 180°, with parts broken away for clarity.

Inner cannula 28 may be of tubular configuration to define an extension 30' of open distal channel 30, as shown in FIG. 3.

Figure 12:
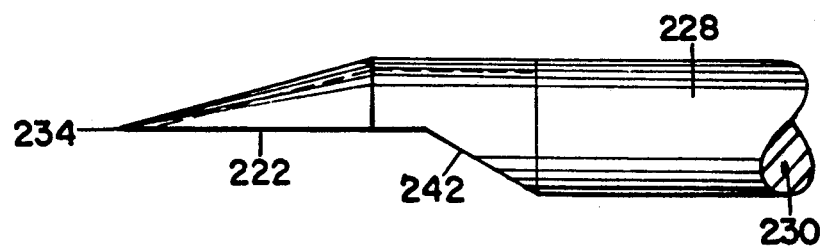
FIG. 12 is a greatly enlarged, fragmentary, top plan view of a second modified form of inner cannula.

Or, as shown in FIG. 12, an inner cannula 228 may be formed as a solid shaft 230 having an integral piercing tip 234, or with the piercing tip welded thereto.

In the FIG. 12 embodiment, the lateral cutting surfaces of piercing tip 234 have been elongated, (only one such surface 222 being shown), to accept larger tissue specimens, and a semi-circular circumferential cutting edge 242 has been inclined rearwardly toward the posterior of the needle at a sharper angle to improve its cutting action.

I claim:

1. A biopsy needle adapted for end cutting, side cutting and extracting of tissue specimens comprising:
    a hand held outer cannula having an open longitudinal channel and a wedge shaped semi-conical hollow piercing tip,
    said piercing tip having an open distal channel in continuity with the open longitudinal channel,
    the wedge shaped hollow piercing tip being defined by two converging lateral cutting surfaces, interconnected inferiorly by a transverse semi-conical base surface,
    and interconnected superiorly by a semicircumferential cutting edge, angled forwardly with reference to the longitudinal axis of the cannula toward the distal end of said cannula,
    a hand held inner cannula telescopically and rotatably fitted within the outer cannula and having an open distal channel co-extensive with the distal channel of the outer cannula, the open distal channels jointly defining a tissue sampling chamber,
    the inner cannula having a semi-conical hollow piercing tip defined by two converging lateral cutting surfaces, interconnected inferiorly by a semi-conical transverse base surface, and superiorly interconnected by a semi-circumferential cutting edge, angled rearwardly toward the posterior of the needle with reference to the longitudinal axis of the cannula, toward the proximal end of said cannula.

2. A method for extracting a tissue specimen from a donor source for diagnostic purposes with the biopsy needle recited in claim 1 comprising three sequential and reversible modes of operation namely,
    a closed-tip piercing operational mode,
    a longitudinal cutting mode and a transverse cutting mode,
    wherein the closed-tip piercing operational mode is achieved through the rotation of the inner cannula within the outer cannula such that they are in an inverse relationship with regard to their geometric features, with such alignment of the cannulas producing an effective conical shape facilitating the piercing of tissue during needle insertion, while avoiding the entrapment of random samples,
    wherein the longitudinal cutting mode is achieved through the rotation of the inner cannula within the outer cannula such that the semiconical distal ends of the cannulas are aligned in a contiguous manner,
    with the tip of the inner cannula fitting precisely within the tip of the outer cannula thereby opening the longitudinal channel within the two cannulas, with longitudinal cutting being accomplished by the two converging lateral surfaces,
    as well as by the forward advancing superior edge, as the needle is advanced in the aforementioned open position into the desired tissue by means of forward motion along the horizontal axis of the biopsy needle,
    and wherein the transverse cutting mode is achieved sequentially following the longitudinal entrapment of specimen tissue through the 180° rotation of the inner cannula within the outer cannula,
    whereby upon completion of the transverse cutting process, the three dimensional specimen is severed and entrapped within the interior diameter of the inner and outer cannulas, whose alignments are now inversely related, with minimized risk of structural damage to the specimen due to crushing or ripping.

3. In the method of claim 2, with said inner cannula performing the transverse cutting of tissue as the outer cannula remains in a stationary position, thereby minimizing traumas to adjacent anatomical structures while enhancing the accuracy of the tissue sample.

4. A method for extracting a tissue specimen from a donor source for diagnostic purposes with a biopsy needle having an inner cannula slidably receivable in and rotational relative to an outer cannula for defining closed piercing/isolating positions and opened severing positions as to each other which comprises:
    a closed conically shaped piercing mode consisting of advancing the closed-position needle to the specimen site,
    an opening wedge-shaped longitudinal cutting mode consisting of rotating the inner cannula in opening rotational direction for opening a specimen chamber within the inner cannula and advancing the needle along the longitudinal needle axis in the longitudinal cutting of the donor source and the leading of the specimen into the specimen chamber,
    a closing transverse cutting mode consisting of rotating the inner cannula in closing rotational direction for effecting the three-dimensional transection of the specimen while the entire needle assembly remains in a stationary position,
    and an extracting mode consisting of withdrawing the inner cannula with the specimen from the outer cannula while said outer cannula remains stationarily fixed within the donor tissue,
    such stationary positioning of the outer cannula securing the sampling accuracy of subsequent specimens by eliminating the possibility of inaccurate re-introduction of the needle assembly.

5. In the method of claim 4 including a repeating mode consisting of returning the inner cannula to its operational position within the outer cannula stationarily fixed within the donor source for a subsequent sampling procedure.

6. In a dual cannula biopsy needle adapted for the longitudinal and transverse cutting of a tissue specimen and separating same from a donor source, the combination of:
    inner and outer cylindrical cannulae with each having a center through passage and a longitudinal axis,
    the inner cannula being axially slidable within and rotational relative to the outer cannula between closed and opened positions,
    the cannulae in closed position cooperatively defining a conical piercing tip,
    each cannula having an open ended configuration for forming a cutting edge in the opened position, the inner cannula defining a sealed specimen chamber within its passage in the closed position, the distal ends of the cannulae being alignable in the opened position to define means effective upon the advancing of the cannulae into the donor source for axially incising a length of the tissue and effective upon the rotation of the inner cannula to closed position for transversely incising the incised length of tissue and severing the specimen from the donor source and isolating same.

7. In a biopsy needle for extracting a tissue specimen from a donor source for diagnostic purposes, the combination of:

an outer cannula having a hollow passage therethrough, an inner cannula having a hollow passage therethrough and being slidably receivable in and rotational relative to the outer cannula, the cannulae defining a closed position when the inner cannula is driven to a stop position in one rotational direction and an opened position when the inner cannula is driven to a stop position in the opposite rotational direction, each cannula having a distal end defining a semi-conical half-section and an opposite opened half section with the opposite sides of the closed half section providing conveying lateral cutting edges toward the outboard termini and interconnected at their inboard termini by an angularized transverse cutting edge, the outboard ends of the cannulae being alignable in the opened position to define means effective upon the advancing of the cannulae into the donor source for axially incising and entrapping a length of the tissue and effective upon the rotation of the inner cannula to closed position for transversely incising the incised length of tissue and severing the specimen from the donor source and isolating same.

8. In a biopsy needle adaptable for the extraction of multiple tissue specimens from a donor source with a single needle insertion and with a minimized risk of trauma to surrounding tissue, the combination of:

outer and inner cannulae each having an open longitudinal central through passage and an open semi-spherical channel in continuity with the central passage and a semi-conical penetrating tip at an outboard end, the cannulae each having converging longitudinal cutting edges on opposite sides of the open channel and having a transverse semi-conical base surface interconnecting inferiorly between the longitudinal cutting edges, the open channel of the outer cannula having a transverse semi-circumferential surface with a cutting edge interconnecting superiorly between the longitudinal cutting edges, the open channel of the inner cannula having a transverse semi-circumferential surface with a cutting edge interconnecting superiorly between the longitudinal cutting edges, the inner cannula being slidable within and rotational about an operative 180° relative to the outer cannula with the cannulae being extendable along a common longitudinal axis between closed and opened position, the cannulae in the closed position jointly defining an exterior conical penetrating tip at the outboard extremity and an interior tissue sampling chamber, the open channels and cutting edges of the cannulae being coextensive and aligned in the opened position, the aligned cutting edges of the cannulae in the opened position defining means effective upon the penetrating of the cannulae into the donor source for axially incising a tissue length and effective upon the rotation of the inner cannula to closed position for transversely cutting the incised tissue length being entrapped within the closing tissue sampling chamber for isolating same with the withdrawal of the inner cannula from the outer cannula.

9. A biopsy needle adapted for end cutting, side cutting and extracting of tissue specimens comprising:

a hand held outer cannula having an open longitudinal channel and a wedge shaped semi-conical hollow piercing tip, said piercing tip having an open distal channel in continuity with the open longitudinal channel, the wedge shaped hollow piercing tip being defined by two converging lateral cutting surfaces, interconnected inferiorly by a transverse semi-conical base surface, and interconnected superiorly by a semicircumferential cutting edge, angled forwardly with reference to the longitudinal axis of the cannula toward the distal end of said cannula, a hand held inner cannula telescopically and rotatably fitted within the outer cannula and having an open distal channel co-extensive with the distal channel of the outer cannula, the open distal channels jointly defining a tissue sampling chamber, the inner cannula having a semi-conical hollow piercing tip defined by two converging lateral cutting surfaces, interconnected inferiorly by a semi-conical transverse base surface, and superiorly interconnected by a semicircumferential cutting edge, angled rearwardly toward the posterior of the needle with reference to the longitudinal axis of the cannula, toward the proximal end of said cannula, the biopsy needle having three sequential and reversible modes of operation namely, a closed-tip piercing operational mode, a longitudinal cutting mode and a transverse cutting mode defined by the procedure of rotating the inner cannula within the outer cannula, wherein the transverse cutting mode is achieved sequentially following the longitudinal entrapment of specimen tissue through the 180° rotation of the inner cannula within the outer cannula, whereby upon completion of the transverse cutting process, the three dimensional specimen is severed and entrapped within the interior diameter of the inner and outer cannulas, whose alignments are now inversely related, with minimized risk of structural damage to the specimen due to crushing or ripping.

10. A biopsy needle as in claim 9, with said inner cannula performing the transverse cutting of tissue as the outer cannula remains in a stationary position, thereby minimizing traumas to adjacent anatomical structures while enhancing the accuracy of the tissue sample.

* * * * *